United States Patent
Silber

(10) Patent No.: US 9,549,678 B2
(45) Date of Patent: Jan. 24, 2017

(54) NON-INVASIVE METHODS AND SYSTEMS FOR ASSESSING CARDIAC FILLING PRESSURE

(75) Inventor: Harry A. Silber, Owings Mills, MD (US)

(73) Assignee: The Johns Hopkins University, Baltimore, MD (US)

( * ) Notice: Subject to any disclaimer, the term of this patent is extended or adjusted under 35 U.S.C. 154(b) by 315 days.

(21) Appl. No.: 13/003,076

(22) PCT Filed: Jul. 1, 2009

(86) PCT No.: PCT/US2009/003935
§ 371 (c)(1),
(2), (4) Date: May 2, 2011

(87) PCT Pub. No.: WO2010/005536
PCT Pub. Date: Jan. 14, 2010

(65) Prior Publication Data
US 2011/0245691 A1    Oct. 6, 2011

Related U.S. Application Data

(60) Provisional application No. 61/134,197, filed on Jul. 8, 2008.

(51) Int. Cl.
*A61B 5/02* (2006.01)
*A61B 5/021* (2006.01)
(Continued)

(52) U.S. Cl.
CPC .............. *A61B 5/021* (2013.01); *A61B 5/0261* (2013.01); *A61B 5/682* (2013.01); *A61B 5/6826* (2013.01);
(Continued)

(58) Field of Classification Search
USPC ........................................................ 600/485
See application file for complete search history.

(56) References Cited

U.S. PATENT DOCUMENTS

| 5,291,895 A | 3/1994 | McIntyre |
| 5,941,837 A * | 8/1999 | Amano ................... A61B 5/024 600/503 |

(Continued)

FOREIGN PATENT DOCUMENTS

| WO | WO 2010/005536 | 1/2010 |
| WO | WO 2011/051819 | 5/2011 |
| WO | WO 2012/155133 | 11/2012 |

OTHER PUBLICATIONS

"Noninvasive Assessment of Central Circulatory Pressures by Analysis of Ear Densitographic Changes During the Valsalva Maneuver" Bernardi et al, Am J Cardiol. Oct. 1, 1989;64(12):787-92 (Bernardi).*

(Continued)

*Primary Examiner* — Michael Kahelin
*Assistant Examiner* — Mitchell E Alter
(74) *Attorney, Agent, or Firm* — Cooley LLP

(57) ABSTRACT

Featured are methods and systems for assessing cardiac filing pressure non-invasively. Such methods include, inter alia, arranging a photoplethysmography (PPG) transducer on a finger of a patient and fluidly coupling a pressure transducer to the patient's mouth so that the pressure transducer measures expiratory pressure. The PPG transducer provides an output of a pulse volume signal of cardiac circulatory flow. Such methods also including determining a pulse amplitude ratio, using the pulse volume near the end of the expiratory effort and a baseline pulse volume, and assessing the pulse amplitude ratio so as to determine a filing pressure condition for the heart of the patient.

18 Claims, 14 Drawing Sheets

(51) Int. Cl.
| | | |
|---|---|---|
| A61B 5/026 | (2006.01) | |
| A61B 5/00 | (2006.01) | |
| A61B 5/0205 | (2006.01) | |
| A61B 5/0215 | (2006.01) | |
| A61B 5/024 | (2006.01) | |

(52) U.S. Cl.
CPC ............ *A61B 5/6838* (2013.01); *A61B 5/0205* (2013.01); *A61B 5/0215* (2013.01); *A61B 5/02416* (2013.01)

(56) References Cited

U.S. PATENT DOCUMENTS

| | | | |
|---|---|---|---|
| 6,162,180 | A | 12/2000 | Miesel et al. |
| 6,228,033 | B1 | 5/2001 | Koobi et al. |
| 6,832,113 | B2 | 12/2004 | Belalcazar |
| 7,195,594 | B2 | 3/2007 | Eigler et al. |
| 2003/0097158 | A1 | 5/2003 | Belalcazar |
| 2004/0019285 | A1* | 1/2004 | Eigler .................. A61B 5/0215 600/488 |
| 2004/0059242 | A1* | 3/2004 | Masuo ................. A61B 5/0537 600/547 |
| 2005/0043767 | A1* | 2/2005 | Belalcazar ...................... 607/30 |
| 2005/0288601 | A1* | 12/2005 | Wood ................... A61B 5/0059 600/513 |
| 2009/0247849 | A1 | 10/2009 | McCutcheon et al. |
| 2010/0069761 | A1 | 3/2010 | Karst et al. |
| 2014/0155764 | A1 | 6/2014 | Silber |

OTHER PUBLICATIONS

"Pulse Pressure Response to the Strain of the Valsalva Maneuver in Humans With Preserved Systolic Function" Hebert, JL et al., J Appl Physiol. Sep. 1998;85(3):817-23, (Hebert).*

Sharma, et al. "Evaluation of a non-invasive system for determining left ventricular end-diastolic pressure," Arch Int Med 2002;162: 2084-89 (Sharma).*

Gillard, C, et al., Operating Characteristics of the Finapress System to Predict Elevated Left Ventricular Filling Pressure, Clin. Cardiol. 29, 107-111 (2006) (Gillard).*

Uehara, H., et al. "A new method of predicting pulmonary capillary wedge pressure: the arterial pressure ratio." Anaesthesia 55.2 (2000): 113-117 (Uehara).*

Silber, Harry A., et al. "Finger photoplethysmography during the Valsalva maneuver reflects left ventricular filling pressure." American Journal of Physiology-Heart and Circulatory Physiology 302.10 (2012): H2043-H2047.*

Bernardi, Luciano, Riccardo Saviolo, and David H. Spodick. "Noninvasive assessment of central circulatory pressures by analysis of ear densitographic changes during the Valsalva maneuver." The American journal of cardiology 64.12 (1989): 787-792.*

International Preliminary Report on Patentability, International Application No. PCT/US2009/003935, dated Jan. 20, 2011.

International Search Report and Written Opinion for Internaional Application No. PCT/US2009/003935, mailed Feb. 23, 2010.

Supplementary European Search Report for European Application No. 12782902.6, mailed Sep. 26, 2014.

International Preliminary Report on Patentability for International Application No. PCT/US2012/037771, dated Nov. 12, 2013.

International Search Report and Written Opinion for International Application No. PCT/US2012/037771, issued Nov. 30, 2012.

Cannesson, M. et al., "Relation between respiratory variations in pulse oximetry plethysmographic waveform amplitude and arterial pulse pressure in ventilated patients," Critical Care, 9(5):R562-R568 (2005).

McIntyre, K. M. et al., "A noninvasive method of predicting pulmonary-capillary wedge pressure," N. Engl. J. Med., 327(24):1715-1720 (1992).

Murray, W. B. et al., "The peripheral pulse wave: information overlooked," Journal of Clinical Monitoring, 12(5):365-377 (1996).

Uehara, H. et al., "A new method of predicting pulmonary capillary wedge pressure: the arterial pressure ratio," Anaesthesia, 55(2):113-117 (2000).

Weilenmann, D., et al., "Noninvasive evaluation of pulmonary capillary wedge pressure by BP response to the Valsalva maneuver," Chest, 122(1):140-145 (2002).

Office Action for U.S. Appl. No. 14/117,079, mailed Nov. 27, 2015.

Anaesthesia UK, "Finapres" [on-line] <URL: http://www.frca.co.uk/article.aspx?articleid=100318#>, Nov. 30, 2004, 2 pages.

Birch, Dr. Tony, "Continuous Non-Invasive Blood-Pressure Measurements," 7th Mathematics in Medicine Study Group, University of Southampton, Sep. 10-14, 2007 [on-line] <URL: http://www.maths-in-medicine.org/uk/2007/blood-pressure/report.pdf>, 18 pages.

Carefirst Bluecross Blueshield, Letter to Harry Silber, MD PhD, dated Apr. 1, 2016 (1 page).

Stony Brook Heart Institute, Letter to Harry Silber, MD PhD, dated Apr. 15, 2016 (1 page).

Wikipedia, "Continuous noninvasive arterial pressure," [on-line] <URL: https://en.wikipedia.org/wiki/Continuous_noninvasive_arterial_pressure>, Aug. 8, 2015, 9 pages.

Final Office Action for U.S. Appl. No. 14/117,079, mailed Sep. 19, 2016.

* cited by examiner

The photoplethysmography signal closely resembles the invasively measured blood pressure signal during the Valsalva maneuver.

NON-INVASIVE METHODS AND SYSTEMS FOR ASSESSING CARDIAC FILLING PRESSURE

RELATED APPLICATIONS/PATENTS & INCORPORATION BY REFERENCE

This application is a 35 U.S.C. §371 U.S. national entry of International Application PCT/US2009/003935 (WO 2010/005536) having an International filing date of Jul. 1, 2009 which claims the benefit of U.S. Provisional Application Ser. No. 61/134,197 filed Jul. 8, 2008, the teachings of which are incorporated herein by reference.

FIELD OF INVENTION

The present invention generally relates to methods and systems for assessing cardiac filing pressure and more particularly to methods and systems for assessing cardiac filing pressure non-invasively.

BACKGROUND OF THE INVENTION

As reported by the New York Heart Association in 2008, heart failure was prevalent in 8.5 million patients in 2008 and this is increasing at an annual growth rate of 10.5%. Thus, by 2010 heart failure can be prevalent in an estimated 11.6 million patients. Further, and as reported by the American Heart Association in 2008, more than 1 million hospital discharges per year have a primary diagnosis of heart failure, the most common discharge diagnosis.

Patients admitted to the hospital with Congestive Heart Failure (CHF) symptoms from severe fluid overload usually have had fluid build-up without symptoms for days or weeks prior to admission. Detection of elevated fluid prior to symptoms could prevent admissions for "acute" decompensated heart failure. Also, many patients with CHF are inadequately diuresed at discharge (i.e., not enough fluid has been removed prior to discharge). This, typically leads to re-admission of the patient for CHF. The rate of rehospitalization for heart failure is very high; about 20% at 30 days after discharge, and about 30% at 60-90 days after discharge.

As is known to those skilled in the art, measurement of left ventricular filing pressure (LVFP) allows detection of CHF and helps assessment of the efficacy of therapy for CHF. Left ventricular pressure can be measured directly by placing a catheter in the left ventricle to obtain the end diastolic pressure (LVDEP) or indirectly by placing a catheter in the pulmonary artery to measure the pulmonary capillary wedge pressure (PCWP). It should be noted that measuring LV filing pressure using a catheter is generally considered the gold standard. The pulmonary artery catheterization (PAC) technique that is used to measure either LVFP or PCWP is considered an invasive surgical procedure. Thus, there are attendants risks and costs associated with such a technique and the reported complications include catheter migration, arrhythmias, pulmonary artery rupture, thrombosis, infection, bleeding and pneumothorax.

Physical examination of a patient has poor sensitivity for detecting elevated cardiac filing pressure, especially in patients with chronic heart failure. Some common aids use to help in the diagnosis of elevated LVFP include chest X-ray, serum biomarkers (BNP, pro_BNP) and echocardiography. These techniques have important practical limitations. Also, clinical and radiographic methods of detecting CHF are generally insensitive to alterations in LVFP.

There have been attempts made to develop a non-invasive method and system for estimating LVFP to allow for early detection and treatment of CHF, which has been shown to reduce the rate of hospitalization and mortality. A non-invasive method of assessing PCWP has been reported that uses the strain phase of the Valsalva maneuver. In a Valsalva maneuver, the subjects or patients perform a forced expiration into a closed tube or strain against a closed glottis. This results in a unique, well-described cardiovascular response, involving both a rise and fall in arterial pressure and a momentary opposite-direction change in right and left heart stroke volume. The effect of the Valsalva maneuver on blood pressure for a normal heart and a heart diagnosed with heart failure is shown in FIG. 1.

In this method a non-invasive pulmonary tonometer and a digital pulmonary monitor is used to continuously acquire arterial and expiratory pressure signals during a Valsalva maneuver. A software program also is used to analyze the arterial pressure signals and derive a LVEDP using a predictive algorithm. The tonomter is not easy to use and is located on the wrist or finger. While this system is not yet commercially available it is expected to cost in the tens of thousands of dollars. The tonometer also is not as widely used a technology as compared to some other medical devices.

Another reported non-invasive technique is referred to as impedance cardiography (ICG). In the ICG technique, four electrodes are placed around the neck and lower thorax and four electrodes are placed on the lateral surface of the abdomen. In this arrangement the outer sensors transmit current and the inner sensors measure impedance. The impedance being measured across the chest is related to fluid volume; thus it can be used to measure changes in fluid volume. However, such measurements do not reflect absolute measurements of LVEDP. The cost for such a device also is in the tens of thousands.

Thus, there is a continuing need to develop non-invasive systems and methods for assessing cardiac filing pressure, more specifically LV filing pressure. It also would be desirable to provide such a device that provides similar useful clinical information as prior art systems and methods. Such systems preferably would be less costly than prior art systems, would use a robust transducer and such methods would not involve or require a greater skill set than that required for user of prior art methods. Moreover, it would be desirable to provide a device or system whose operation is simple enough for a patient or the like to use at home.

SUMMARY OF THE INVENTION

The present invention features methods and systems for assessing cardiac filing pressure non-invasively. In its broadest aspects, such methods include coupling a device configured to non-invasively measure pulse changes in pulse volume to a patient or subject and fluidly coupling a pressure transducer to the patient's mouth so that the pressure transducer measures expiratory pressure. Such methods also include determining a pulse amplitude ratio, using the pulse amplitude near the end of the expiratory effort and a baseline pulse amplitude, and assessing the determined pulse amplitude ratio so as to determine a filing pressure condition for the heart of the patient.

In more particular embodiments, such methods include arranging an optical volume sensing device such as a photoplethysmography (PPG) transducer on a finger or digit of a patient or subject, and fluidly coupling a pressure transducer to the patient's mouth so that the pressure transducer measures expiratory pressure. When so arranged the optical pulse volume sensing device such as a PPG senses a change in volume caused by the pressure pulse, by illuminating the skin with light from an LED and then measuring the amount of light either transmitted or reflected to a photodiode. The optical pulse volume sensing device provides an output of a pulse volume signal of cardiac circulatory flow.

Such methods also include determining a pulse amplitude ratio, using the pulse amplitude near the end of the expiratory effort and a baseline pulse amplitude, and assessing the determined pulse amplitude ratio so as to determine a filing pressure condition for the heart of the patient.

In yet further embodiments, such fluidly coupling includes providing a mouth piece and/or tubing one end of which is fluidly coupled to the patient's mouth and where the pressure transducer is disposed in one of the mouth piece or tubing so the pressure transducer is remote from the mouth.

In yet further embodiments, such methods include providing a microprocessor, or a computer including such a microprocessor, and communicatively coupling the microprocessor to each of the pressure transducer and the optical pulse volume sensing device (e.g., PPG). The microprocessor determines the pulse amplitude ratio from the signals from the pressure transducer and the optical pulse volume sensing device (e.g., PPG).

In yet further embodiments, such methods further include providing an applications program including program segments and instructions and criteria for carrying out the methods of the present invention, including periodically determining the pulse amplitude ratio. In further embodiments, such an applications program includes program segments and instructions and criteria for causing the periodically determined pulse amplitude ratios as well as any other data such as the pulse pressure near the end of the expiratory effort, the baseline pulse pressure and measured expiratory pressures, to be stored in a storage device.

In yet further embodiments, such methods further include providing a printing device for printing of information and operably coupling the provided microprocessor or the computer to the provided printing device.

In yet further embodiments, such methods further include providing a device including an enclosure, the microprocessor and storage device, where the microprocessor and storage device are disposed within the enclosure so that the device is one of free-standing, on a rolling cart or portable so as for example, the device can be carried in the pocket of a jacket worn by the clinician, technician or medical personnel.

In yet further embodiments, the provided device is configured and arranged so as to be in a form that is usable by a patient or other persons that do not have specific medical training outside a clinical setting (e.g., the home of a patient) and without the aid or guidance of a clinical practitioner or other medical personnel, or usable by medical personnel (e.g., visiting nurse or nursing aid) outside the clinical setting (e.g., patient's home). For example, the provided device can be configured so as to display instructions to the patient or the not medically trained personnel although in alternative embodiments, printed instructions can be provided with the device. Also, the provided device can be configured so as to display information as to how to conduct the testing protocol such as for example, displaying the desired expiratory pressure to reach, the time period for maintaining such an expiratory pressure and how and where the leads should be connected to the body.

In yet further embodiments, the provided device is configured and arranged so as to include a positive pressure delivery device that delivers a specified amount if inspiratory pressure to a patient instead of having the patient exhale in a described manner. The microprocessor would determine the pulse amplitude ratio from the signals from the pressure transducer and the optical pulse volume sensing device (e.g., PPG). Such a positive pressure delivery device is advantageous as it would allow a patient to be tested, even at home with supervision, when the patient cannot follow directions for any of a number of reasons to allow testing using a Valsalva maneuver or is otherwise able to perform such a maneuver for the time periods required for such testing.

In yet further embodiments, the provided device is configured and arranged so the provided device can provide information to allow the clinician to make a determination or ascertain central arterial stiffness of the patient. Some studies have shown that central arterial stiffness can affect the Pulse Amplitude Ratio. Thus, taking into account central arterial stiffness can improve the accuracy of the device for evaluating cardiac filling pressure. In exemplary embodiments, the provided device includes a second photoplethysmography (PPG) transducer that is located on/attached to a toe of the patient, or an ECG signal lead that is attached to one finger of each hand. Either of these two, provided a mechanism for ascertaining central arterial stiffness.

In yet further embodiments, the provided device also is configured and arranged with one or more communication interfaces so that the user of the device (e.g., patient, practitioner, visiting nurse, technician, clinical personnel) can easily transmit or communicate the data acquired and/or determined using the device (i.e., acquired information), directly or ultimately to the practitioner who should receive such clinical information. For example, the information being transmitted can be communicated directly to a computer or storage device under the control of the practitioner or to a monitoring service that subsequently transmits the acquired information to the practitioner also using any of a number of techniques known to those skilled in the art. For example, data can be acquired by a monitoring service in a clinical setting or from patient home and then communicated to the practitioner or their office.

In more particular embodiments, the one or more communication interfaces provide a mechanism by which the device can be communicatively coupled to any of a number of communication systems known or hereinafter created so that the acquired information can be transmitted or communicated over such a communication system. For example, communication can occur over a telephone phone system where the device is communicatively coupled to the system via a hard land line (e.g., copper, optical) or a wireless connection. Also for example, the provided device can be communicatively coupled to a network (e.g., WAN, LAN WiFi) by a hard line or wireless such that acquired information can be communicated via the network to a monitoring station or a device (e.g., computer) associated with the practitioner. In further embodiments, the network can be operably coupled to the internet so that information is communicated via the network and/or internet to the monitoring service or the practitioner. Also, in the case where the provided device is a non-clinical setting, the communication interface and provided device are configurable so that the user can couple the provided device to the patient's internet connection so that acquired information can be transmitted or communicated via that connection to the monitoring service or practitioner.

In yet further embodiments, the device is arranged so as to include one of a display or a printing device so that the determined information is one of displayed to the user or a hard copy of the determined information is printed out for the user. In more particular embodiments, such displaying or printing is done one of automatically or in response to an input from the user.

In more particular embodiments, the device includes means for communicatively coupling the device microprocessor to each of the optical pulse volume sensing device and the pressure transducer (e.g., via wires, cables, wireless communication devices).

In yet further embodiments, such methods further include providing a real-time pressure display operably coupled to the pressure transducer and directing the patient or subject to control the expiration pressure being displayed to be at one of a plurality of different values. In more particular embodiments, such methods include obtaining a plurality of pulse amplitude ratios, where at least one of the plurality pulse amplitude ratios is determined under a different expiratory pressure.

In further particular embodiments, the expiratory pressure condition is maintained for a period of 10 or more seconds or 10 or less seconds, or about 10 seconds or in the range of from about 8 to about 12 seconds. In yet further particular embodiments, the expiratory pressure condition is maintained at about 20 mmHg, or at least 20 mmHg, or in the range of from about 20 mmHg to about 35 mmHg, or in the range of from about 10 mmHg to about 50 mmHg. In the case where a plurality of pulse amplitude ratios are obtained and where at least one of the plurality of pulse amplitude ratios is determined under a different expiratory pressure; each of the different expiratory pressures is in the range of from about 10 mmHg to about 50 mmHg.

In further embodiments, when the device is configured with a positive pressure delivery device, instead of maintaining the expiratory pressure condition for the above described periods, such methods include controlling the positive pressure delivery device so the pressurized inspiratory pressure is maintained for the described time periods and/or controlling the positive pressure delivery device so that different pressurized inspiratory pressure conditions are established within the range of pressure conditions.

In yet further embodiments, such methods further includes acquiring information to allow an assessment to be made of arterial stiffness.

Systems for assessing cardiac filing pressure non-invasively embody the features and functionalities for carrying out the functions described above. In illustrative embodiments such a system includes an optical pulse volume sensing device, configured and arranging so as to be located on a finger or digit of a patient or subject and so that the optical pulse volume sensing device senses a change in volume cause by the pressure pulse; and a pressure transducer that is configured and arranged so as to be fluidly coupled to a mouth of the patient and so that the pressure transducer measures expiratory pressure. Such a system also includes means for determining a pulse amplitude ratio, using the pulse amplitude near the end of the expiratory effort and a baseline pulse amplitude, and means for assessing the determined pulse amplitude ratio so as to determine a filing pressure condition for the heart of the patient.

In further embodiments, the means for determining a pulse amplitude ratio and the means for assessing the determined pulse amplitude ratio includes a microprocessor and means for communicatively coupling the microprocessor to each of the pressure transducer and the optical pulse volume sensing device, and an applications program for execution on the microprocessor. The applications program includes program segments and instructions and criteria for determining the pulse amplitude ratio from the output signals from the pressure transducer and the optical pulse volume sensing device.

Also featured is a device for assessing cardiac filing pressure of a patient non-invasively. In illustrative embodiments such a device includes an optical pulse volume sensing device, configured and arranging so as to be located on a finger or digit of a patient or subject and so that the optical pulse volume sensing device senses a change in volume caused by the pressure pulse, a microprocessor and means for communicatively coupling the microprocessor to the optical pulse volume sensing device and to a pressure transducer that is fluidly coupled to a mouth of the patient so that the pressure transducer measures expiratory pressure.

Such a device also includes an applications program for execution on the microprocessor. The applications program includes program segments and instructions and criteria for determining a pulse amplitude ratio, using the pulse amplitude near the end of the expiratory effort and a baseline pulse amplitude; and for assessing the determined pulse amplitude ratio so as to determine a filing pressure condition for the heart of the patient.

In further embodiments, the device further includes a display device and/or a printing device; each of the display device and printing device being operably coupled to the microprocessor. The display device is configured and arranged so as to display determined information to the user and the printing device is configured and arranged so as to output a hard copy of the determined information to the user. Also, the applications program further includes program segments and instructions and criteria for causing the one of the display device or printing device to respectively display or output the determined information.

Other aspects and embodiments of the invention are discussed below.

DEFINITIONS

The instant invention is most clearly understood with reference to the following definitions.

The acronym CHF shall be understood to mean congestive heart failure.

The acronym LV shall be understood to mean the left ventricle of a heart.

The acronym LVFP shall be understood to mean left ventricular filing pressure.

The acronym LVDEP shall be understood to mean the end diastolic pressure in the left ventricle, which can be measured by placing a catheter in the left ventricle.

The acronym PCWP shall be understood to mean pulmonary capillary wedge pressure, which can be measured by placing a catheter in the pulmonary artery.

The acronym PAC shall be understood to refer to the pulmonary artery catheterization technique, a technique used to measure for example LVFP or PCWP.

The acronym PPG shall be understood to mean photoplethysmography. Photoplethysmography is a determination in which the intensity of light reflected from the skin surface and the red cells below is measured to determine the blood volume of the respective area. There are two types, transmission and reflectance.

BRIEF DESCRIPTION OF THE DRAWING

For a fuller understanding of the nature and desired objects of the present invention, reference is made to the following detailed description taken in conjunction with the accompanying drawing figures wherein like reference characters denote corresponding parts throughout the several views and wherein.

DESCRIPTION OF THE PREFERRED EMBODIMENT

Figure 2:
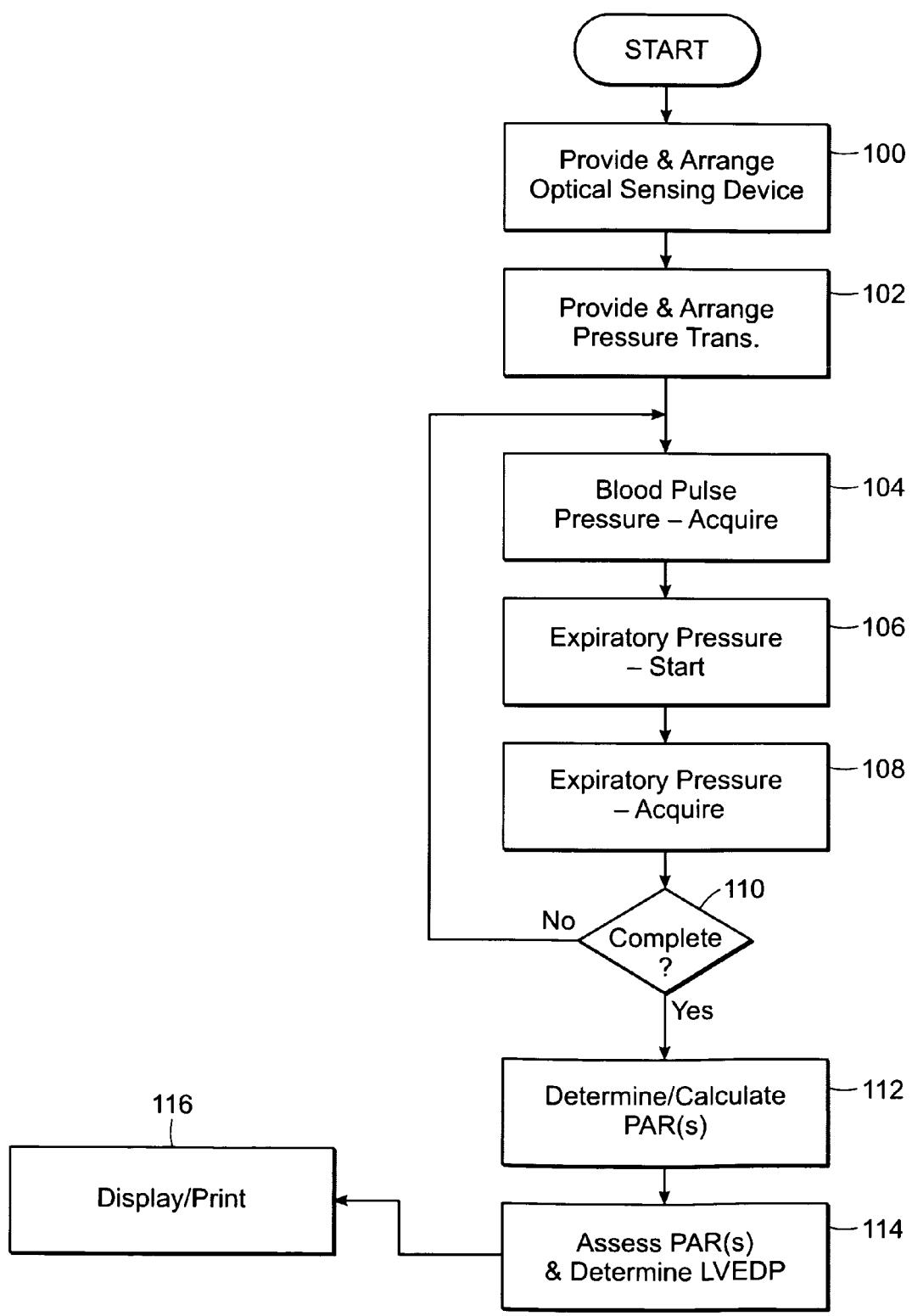
FIG. 2 is a high level flow diagram of a methodology for assessing cardiac filing pressure non-invasively according to the present invention.

Referring now to the various figures of the drawing wherein like reference characters refer to like parts, there is shown in FIG. 2 a high level flow diagram of a methodology for assessing cardiac filing pressure non-invasively according to the present invention. Reference also should be made to FIGS. 3A-D which illustrate various block diagrams of systems 200a-d for assessing cardiac filing pressure non-invasively according to the present invention that can include details and features not shown in FIG. 2. Reference also should be made to FIGS. 3E-H which are various block diagrams illustrating various ways in which a system 200 or a device embodying such a system (whole or in part) along with one of a number of communication techniques whereby the system or device can transmit or communicate information to for example, the practitioner or a monitoring service.

Before describing the methodology, the illustrative composition of such each system 200a-d of the present invention is first described.

Figure 3A:
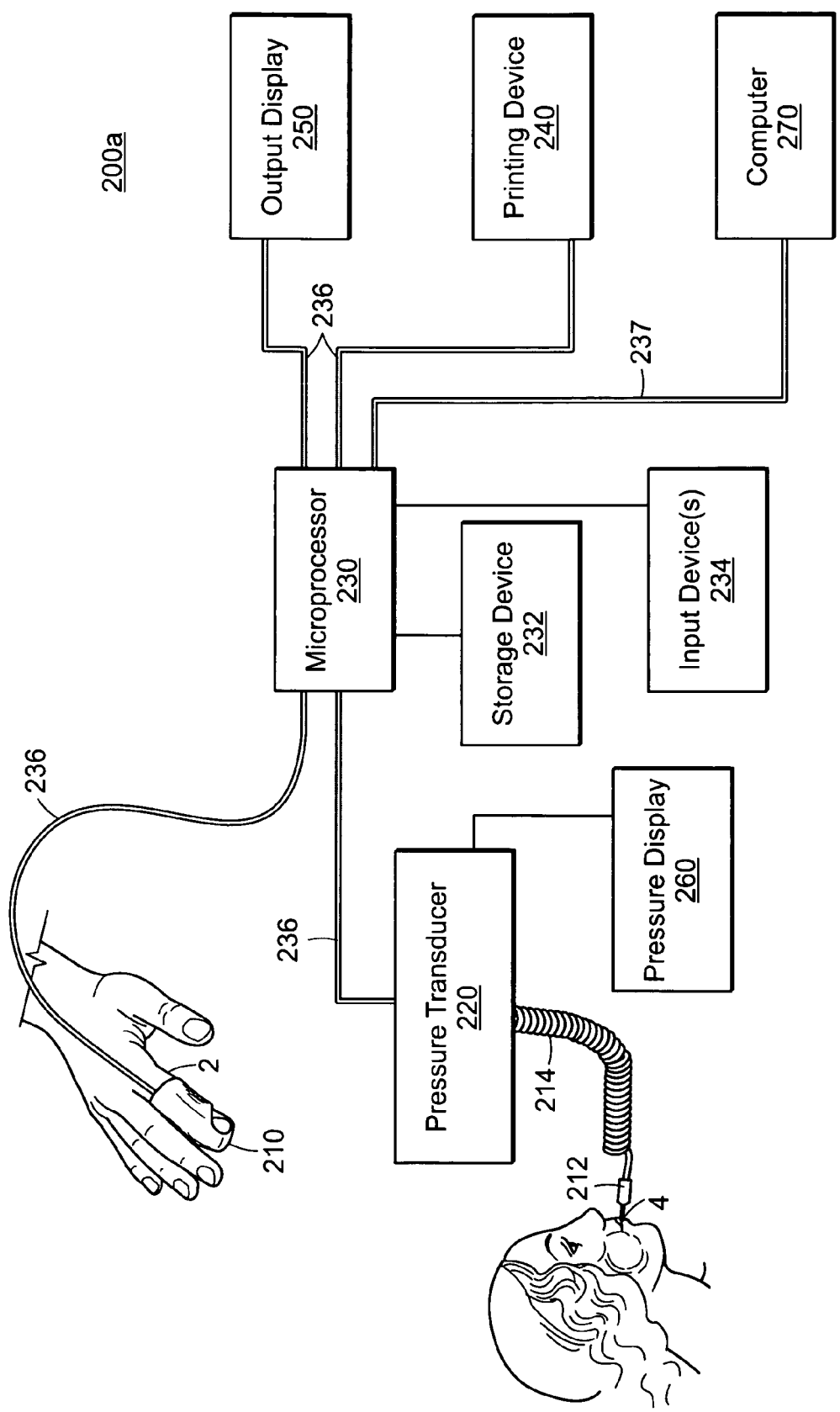
FIG. 3A is a block diagram of an exemplary system for assessing cardiac filing pressure non-invasively according to the present invention.

Referring now to FIG. 3A, such a system 200a includes an optical pulse volume sensing device 210, a pressure transducer 220, a means for determining a pulse amplitude ratio, using the pulse amplitude as determined from output signals from the optical pulse volume sensing device near the end of the expiratory effort as determined from the outputs from the pressure transducer and a baseline pulse amplitude as determined from output signals from the optical pulse volume sensing device, and means for assessing the determined pulse amplitude ratio so as to determine a filing pressure condition for the heart of the patient. The optical pulse volume sensing device 210 is configured and arranging so it can be located on, and removably secured to, a finger 2 or digit of a patient or subject and so that the optical pulse volume sensing device senses a change in volume cause by the pressure pulse. The pressure transducer 220 is configured and arranged so as to fluidly coupled to a mouth 4 of the patient and so that the pressure transducer measures expiratory pressure of such a patient. In exemplary embodiments, the optical pulse volume sensing device 210 is a photoplethysmography (PPG) transducer and the pressure transducer 220 is any of a number of devices known to those skilled in the art and appropriate for the intended use.

In particular embodiments, the pressure transducer 210 is operably coupled to a mouth piece 212 and/or tubing 214, so that the pressure transducer is remote from the patient's mouth 4. One end of the mouth piece 212 or the tubing 214 is fluidly coupled to the mouth. In an exemplary embodiment, one end of the mouth piece 212 is removably fluidly coupled to the mouth using any of a number of techniques known to those skilled in the art and the other end of the mouth piece and an end of the tubing are fluidly coupled or joined to each other to form a unitary structure.

Figure 3B:
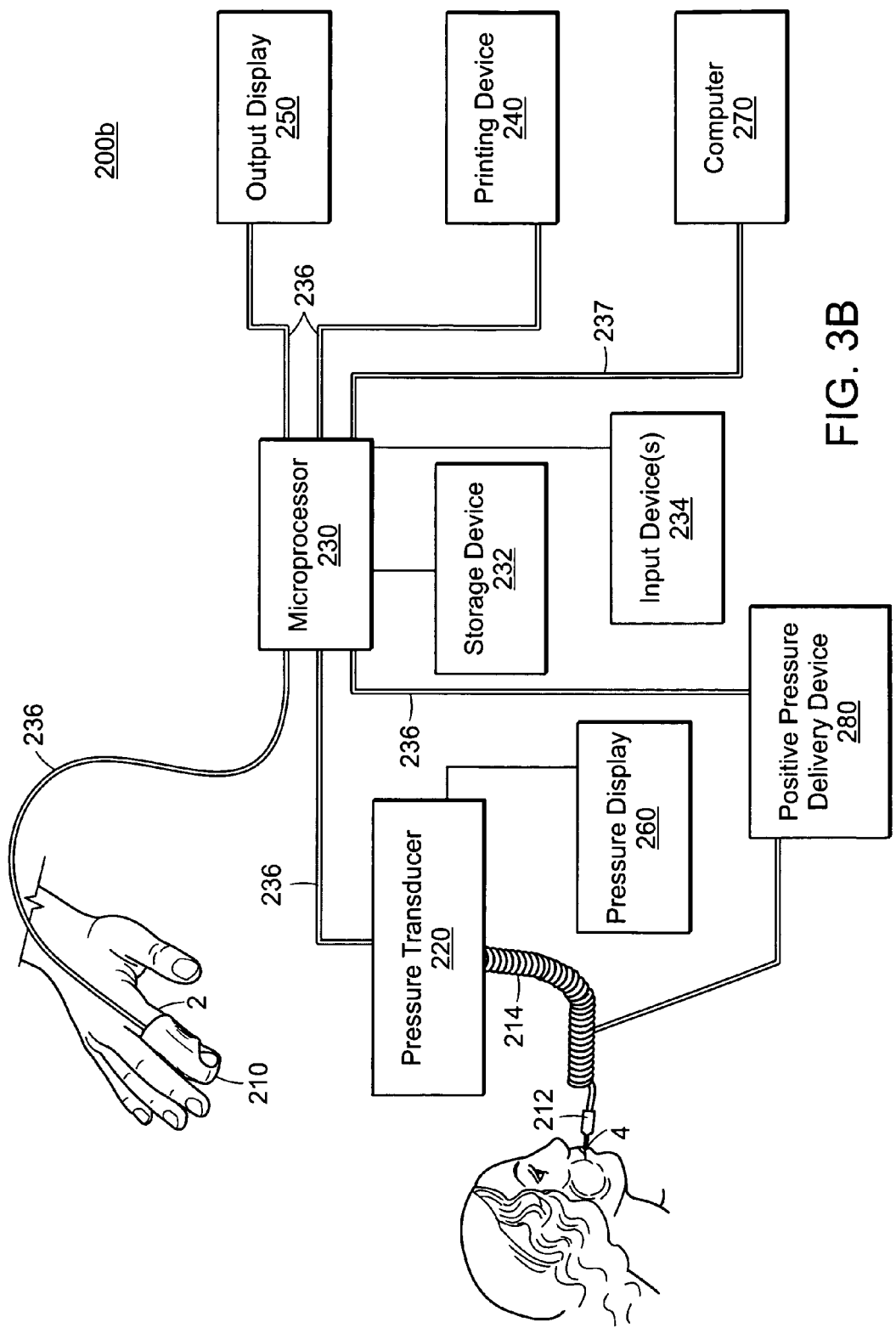
FIG. 3B is a block diagram of another exemplary system for assessing cardiac filing pressure non-invasively according to the present invention.

Referring now to FIG. 3B, there is shown another system 200b according to the present invention that is configured and arranged so as to include a positive pressure delivery device 280 that is selectively fluidly coupled to the tubing 214 and operably and/or communicatively coupled to the microprocessor 230. The microprocessor 230 controls the positive pressure delivery device 280, so that a pressurized breathing gas mixture (e.g., air) is delivered to the patient via the tubing 214 for a predetermined period of time, such as those times described herein for the expiratory pressure. In yet further embodiments, the microprocessor 230 controls the positive pressure delivery device 280, so that a pressurized breathing gas mixture of different pressures are delivered to the patient. In exemplary embodiments, the a positive pressure delivery device 280 includes a source of the breathing mixture (e.g., tank, or connection to a delivery system) and a valve that is interposed between the breathing mixture source and the tubing 214. The valve is operably coupled to the microprocessor 230, whereby the microprocessor controls the valve for selectively delivering the breathing mixture to the patient. In further embodiments, the valve also is of the type that is controllable so as to deliver gas mixtures at different pressures.

Figure 3C:
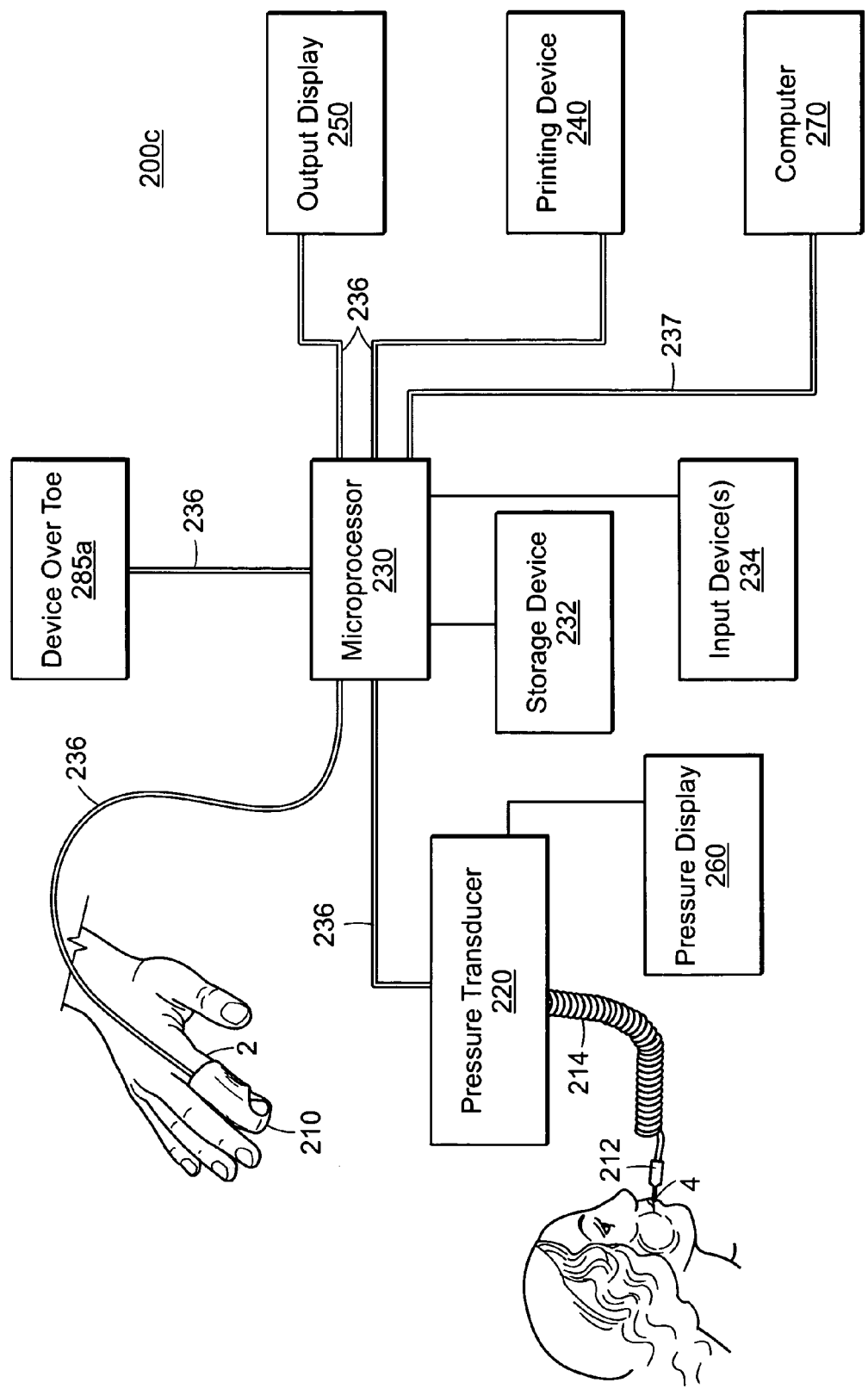
FIG. 3C is a block diagram of yet another exemplary system for assessing cardiac filing pressure non-invasively according to the present invention.
Figure 3D:
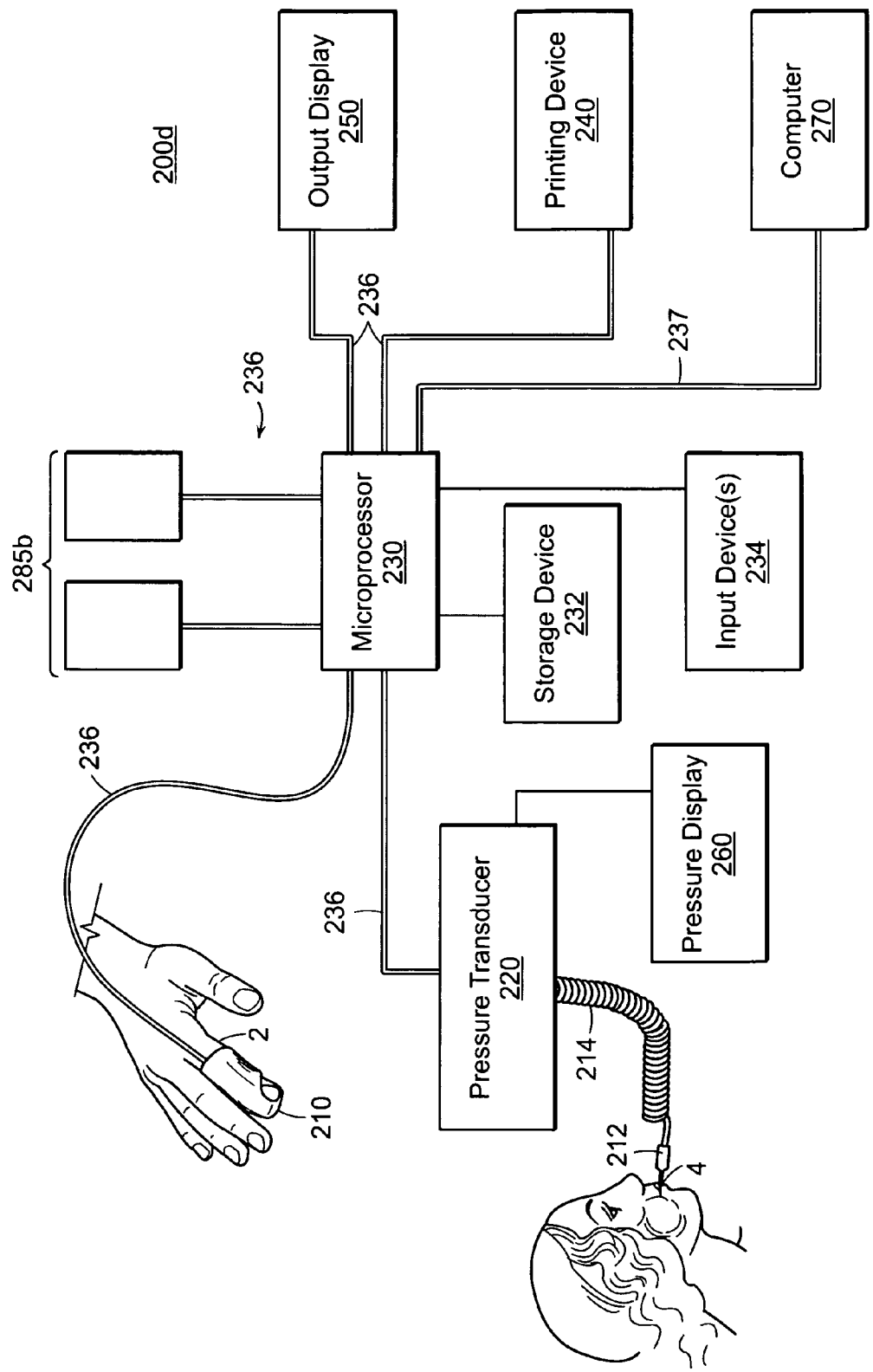
FIG. 3D is a block diagram of yet another exemplary system for assessing cardiac filing pressure non-invasively according to the present invention.

Referring now to FIGS. 3C, D there are shown to exemplary systems 200b-c that further include a device 285a,b that allows the device to acquire information that the clinician can use to assess or determine the arterial stiffness or central arterial stiffness (e.g., the pulse wave velocity, PWV) of the patient. Some studies have shown that central arterial stiffness can affect the Pulse Amplitude Ratio. Thus, taking into account central arterial stiffness can improve the accuracy of the device for evaluating cardiac filling pressure.

In exemplary embodiments, the device is another photoplethysmography (PPG) transducer 285a (FIG. 3C) that is located on or attached to a toe of the patient. In yet another exemplary embodiment, an ECG signal lead 285b (FIG. 3D) is attached to one finger of each hand. Either of these two, provided outputs that in combination with any of a number of techniques known to those skilled in the art provides a mechanism by which the clinician can ascertain the central arterial stiffness of the patient.

In illustrative embodiments, the means for determining a pulse amplitude ratio and the means for assessing the determined pulse amplitude ratio are embodied in a microprocessor 230 that is communicatively coupled to each of the pressure transducer 220 and the optical pulse volume sensing device 210. The functionalities are coupled by cables 236 as is known to those skilled in the art and appropriate for the intended use (e.g., electrical cables, optical cables). Such a microprocessor 230 includes random access memory, cache and other functionalities (not shown) that allow the microprocessor to function in the intended manner. In yet further embodiments, the microprocessor 230 is embodied in any of a number of computers as are know to those skilled in the art.

An applications program for execution on the microprocessor 230 is provided, which applications program controls operation of the system and the microprocessor. It is within the skill of those knowledgeable in the computer or software arts to develop such an applications program based on the disclosure herein, including the following discussion regarding the methodology of the present invention. In particular, the applications program includes program or code segments and instructions and criteria for determining the pulse amplitude ratio from the output signals from the pressure transducer and the optical pulse volume sensing device.

One or more storage devices 232 are operably coupled to the microprocessor 230 for storage of, for example, the applications program, the operating system and any data or input information as directed by the user and/or the applications program. Such a storage device is any of a number of devices known to those skilled in the art and includes magnetic hard drives, and flash storage devices that embody flash or non-volatile flash memory. Also operably coupled to the microprocessor 230 is/are one or more input devices 234 such as a keyboard and/or mouse that allow the user to control operation of the microprocessor.

In the case where the microprocessor 230 is not embodied in a computer, the microprocessor 230 is further configured and arranged so it can be operably coupled to a computer 270, for example via removable cables 237 (e.g., USB cables). In this way, information temporarily stored in the storage device 232 can be uploaded to the computer for further analysis and/or long term storage or to allow communication of data and information to another via a network, an external communication system or via a recording medium (e.g., optical disk, magnetic recording medium).

In further embodiments, the microprocessor 230 also is operably coupled to a an output display 250 and a printing device 240. The output display 250 is any of a number of display devices as are known to those skilled in the art or hereinafter developed that are appropriate for inter connection with a microprocessor and for displaying information thereon that is communicated from the microprocessor. The printing device 240 is any of a number of devices as are known to those skilled in the art or hereinafter developed that are appropriate for inter connection with a microprocessor and for printing information there from and communicated from the microprocessor.

In embodiments or aspects of the present invention, the microprocessor 230 and other functionalities of the systems 200a-d are intended to be disposed within any of a number of enclosures known to those skilled in the art to form a device, which device has varying degrees of portability, for example, from being located on a rolling cart to being put in the coat of the medical personnel using the device. As such, the output display 250 and/or printing device 240 also can be any of a number of devices that can be co-located in such an enclosure with the microprocessor 230 and other functionalities of the system 200a-d. There are a number of devices or existing platforms known to those skilled (e.g., Wellch Allyyn Spot Vital Signs Model 42NOB-E1) which acquire acquiring patient data and which are operably coupled to an optical pulse volume sensing device. Thus, it also is contemplated and thus within the scope of the present invention to adapt such existing platforms or devices so as to carry out any functions described herein for the systems 200a-d of the present invention.

The systems of the present invention also are configurable so that is free-standing, on a rolling cart, or portable. Such systems also are configurable so that it can be used in an outpatient clinic, an emergency department, a medical ward, an intensive care unit, skilled care facilities, assisted living facilities, or home or used by home services such as for example a visiting nursing service.

In further embodiments, such a system 200a-d further includes a pressure display 260 that is operably coupled to the pressure transducer 220 so as to provide a local display of the expiratory pressure/pressurized inspiratory pressure. Such a display is used by the medical personnel and/or the patient to determine that the expiratory pressure of the patient is at the value desired for a given measurement process. Thus, the pressure display 260 is any of a number of digital or analog displays or pressure measurement devices that are appropriate for the intended use and anticipated pressures or pressure ranges. In more particular embodiments, the pressure display 260 is configurable so as to further provide a display of elapsed time.

In yet further embodiments, the system 200a-d is embodied in an enclosure so as to from a portable device, where the device is further configured and arranged so as to be in a form that is usable by a patient or other persons that do not have specific medical training outside a clinical setting (e.g., the home of a patient) and without the aid or guidance of a clinical practitioner or other medical personnel, or the device is usable by medical personnel (e.g., visiting nurse or nursing aid) outside the clinical setting (e.g., patient's home). For example, the provided device can be configured so as to display instructions to the patient or other person who are not medically trained although in alternative embodiments, printed instructions can be provided with the device. Also, the provided device can be configured so as to display information as to conducting the testing protocol or procedure such as for example, displaying the desired expiratory pressure to reach, the time period for maintaining such an expiratory pressure and how and where the leads should be connected to the body.

In yet further embodiments, the provided device also is configured and arranged with one or more communication interfaces 310 so that the user of the device (e.g., patient, practitioner, visiting nurse, technician, clinical personnel) can easily transmit or communicate the data acquired and/or determined using the device (i.e., acquired information), directly or ultimately to the practitioner who should receive such clinical information. For example, the information being transmitted can be communicated directly to a computer or storage device under the control of the practitioner or to a monitoring service that subsequently transmits the acquired information to the practitioner also using any of a number of techniques known to those skilled in the art. For example, data can be acquired by a monitoring service in a clinical setting or from patient's home and then communicated to the practitioner or their office.

In more particular embodiments and with reference to FIGS. 3E-H, the one or more communication interfaces 310a-d provide a mechanism by which the device 300a-d can be communicatively coupled to any of a number of communication systems known or hereinafter created so that the acquired information can be transmitted or communicated over such a communication system.

Figure 3E:
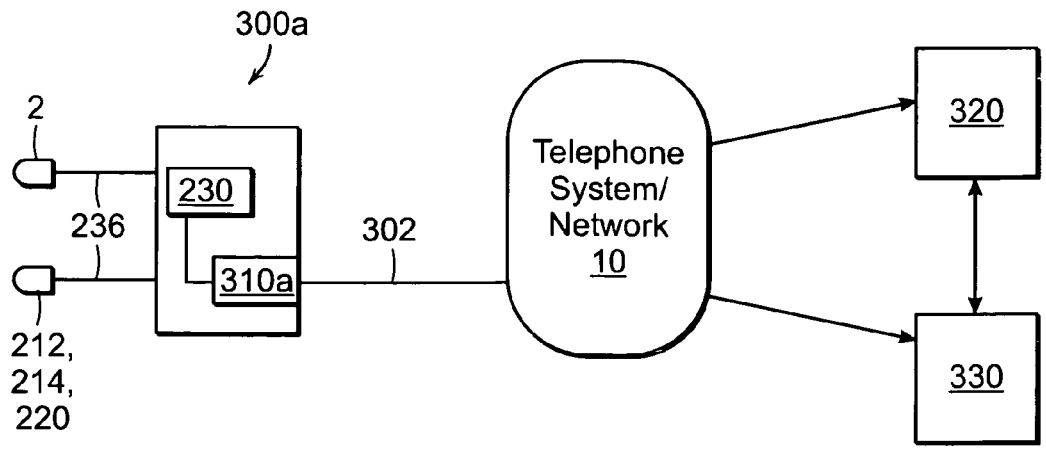
FIGS. 3E-H are various block diagrams illustrating a device according to the present invention used in various communication environments.

Referring now to FIG. 3E, there is shown one exemplary device 300a according to the present invention that includes an interface 310a, such as a modem or equivalent, which is operably coupled to the microprocessor 230 and to a telephone phone system 10 via a hard land line 302 (e.g., copper, optical). As is known to those skilled in the art, such an interface 310 is configured an arranged so that the microprocessor can communicate information over the telephone system 10 to another device that is similarly operably coupled to the telephone system. In this way, the clinical information obtained using the device 300a can be communicated to one or both of the practitioner 320 or a monitoring service 330 via the telephone system. As illustrated in FIG. 3E, the monitoring service is communicatively coupled to the practitioner using any of a number of communication techniques know to those skilled in the art.

Figure 3F:
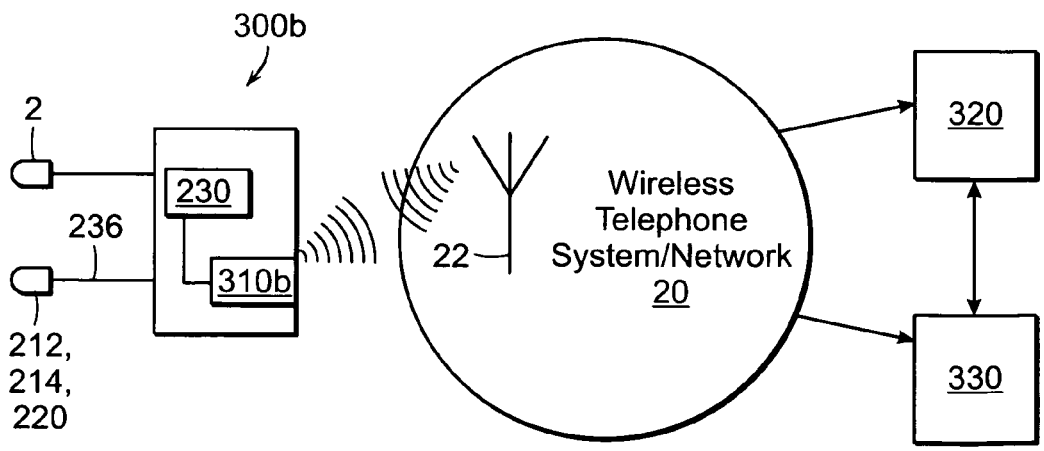

Referring now to FIG. 3F, there is shown a second exemplary device 300b that includes an interface 310b as is known to those skilled in the telephone arts for wirelessly (e.g., using RF transmissions) coupling the second exemplary device 300b to a wireless telephone system 20. As is known to those skilled in the art, such a wireless telephone system 20 includes an antenna 22 or tower that receives the signals from a wireless device and also can be coupled to a wired telephone system or another wireless telephone system so as to allow a communication link between the second exemplary device 300b and another device. Such an interface 310b is operably coupled to the microprocessor 230 and generally includes an antenna so that wireless (RF) signals pass between the wireless telephone phone system 20 and the exemplary second device 300b.

As is known to those skilled in the art, such a wireless interface 310b allows the microprocessor 230 to communicate information via RF transmission to/from the telephone system 20 and thus onto another device that is similarly operably coupled to the telephone system. In this way, the clinical information obtained using the device 300b can be communicated to one or both of the practitioner 320 or a monitoring service 330 or monitoring apparatus via the telephone system. As illustrated in FIG. 3F, the monitoring service is communicatively coupled to the practitioner using any of a number of communication techniques know to those skilled in the art.

Figure 3G:
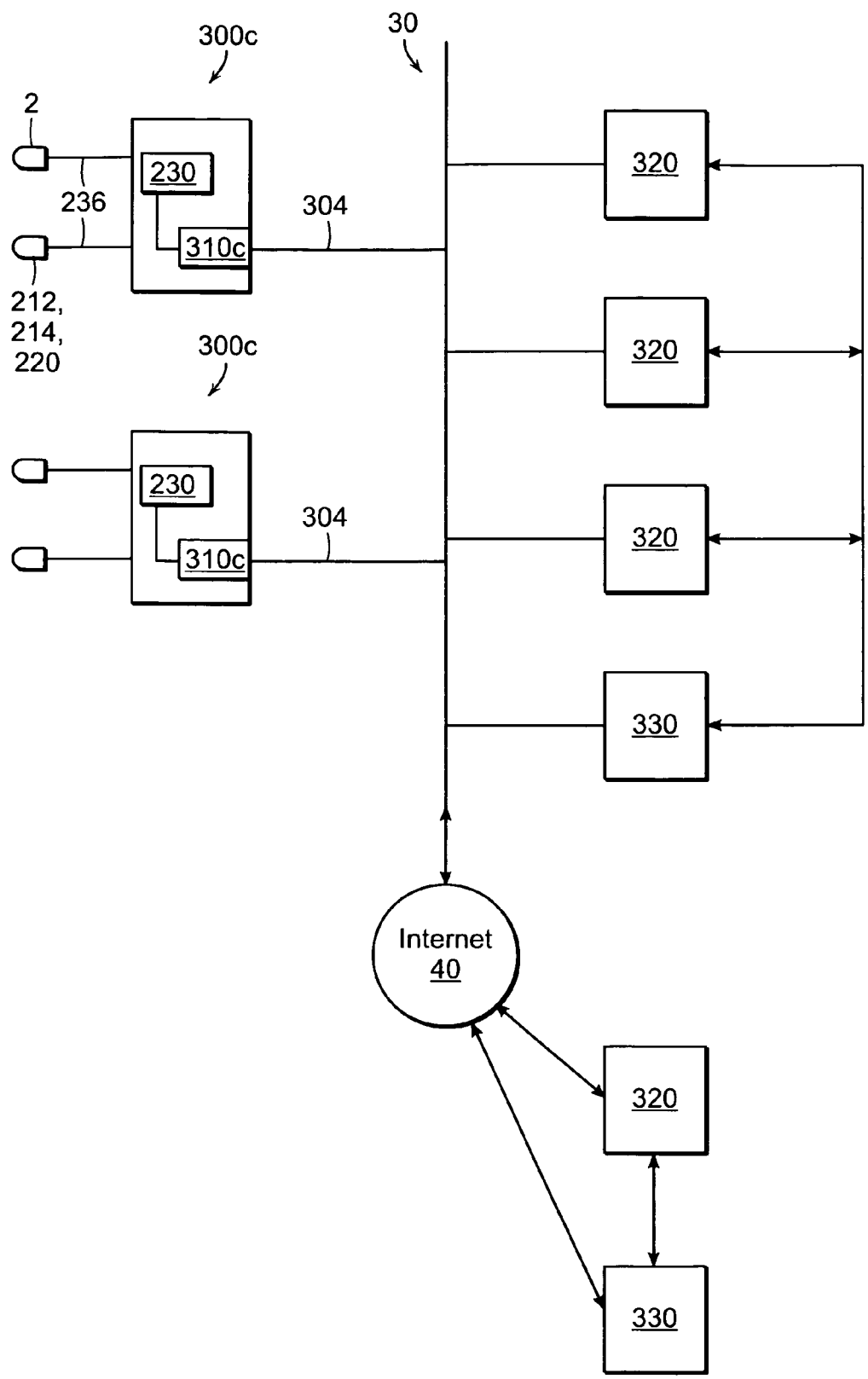

Referring now to FIG. 3G, there is shown a third exemplary device 300c that includes an interface 310c for communicatively coupling the third exemplary device to a network 30 (e.g., WAN, LAN), which in turn can be communicatively coupled to the internet 40. In the illustrated embodiment, the interface 310c is any of a number of devices as is known to those skilled in the art so that the device can be communicatively coupled via a hard line 304 (e.g., optical, copper, shielded cable).

Figure 3H:
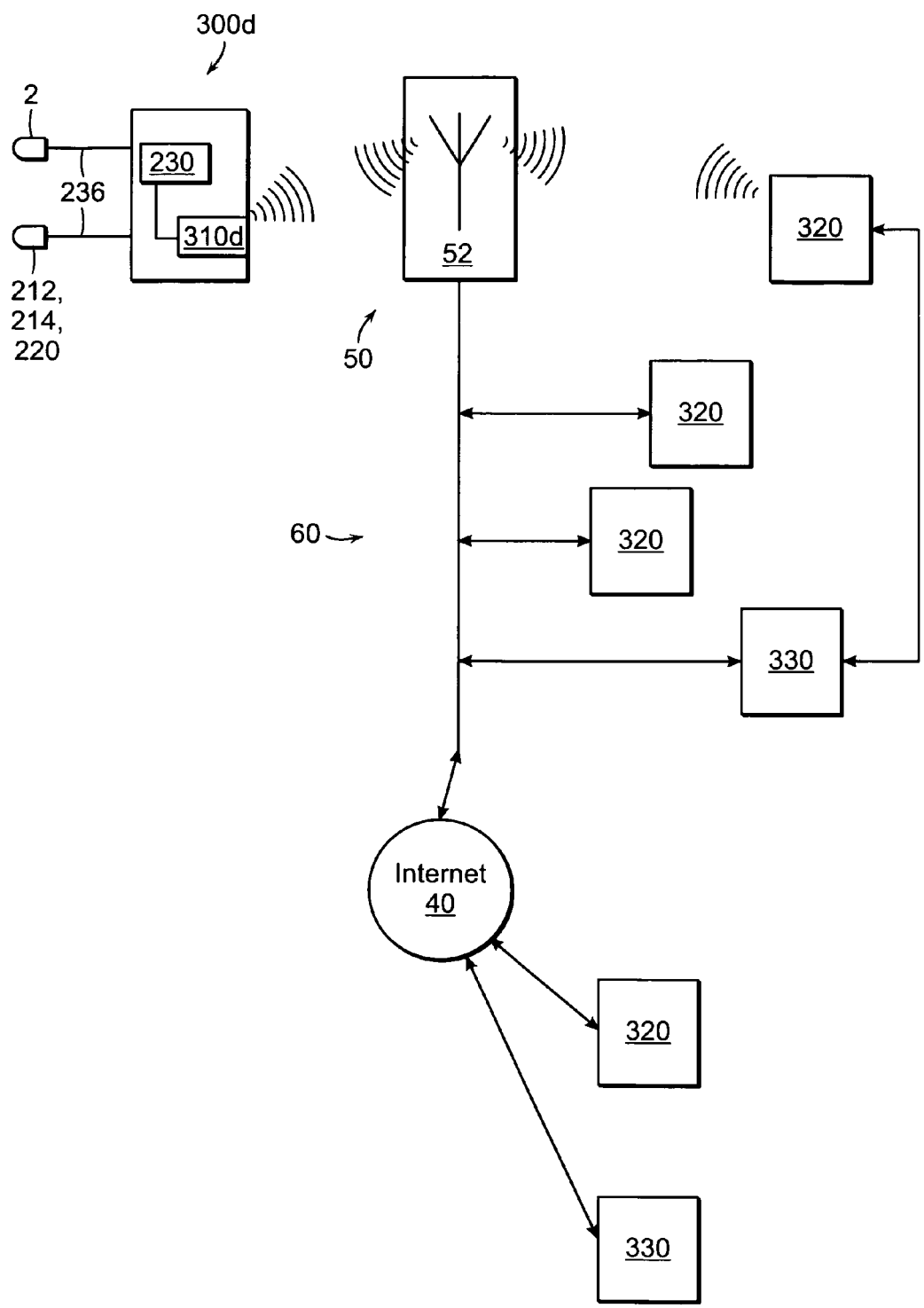

In alternative embodiments and with reference to FIG. 3H, there is shown a fourth exemplary device 300d including an interface 310d that is configured and arranged to communicate with a wireless hub or router 52 so as to thereby create a wireless network 50. In further embodiments, the wireless network 50 is a part of a larger network 60. In yet further embodiments, a plurality of devices 300c can be coupled to either network 30, 50, 60 at any time.

As is known to those skilled in the art, such interfaces 310 c,d are configured an arranged so that the microprocessor 230 can communicate information over a complimentary network 30, 50, 60 to another device that is similarly operably coupled to the network. In this way, the clinical information obtained using either of the devices 300 c,d can be communicated to one or both of the practitioner 320 or a monitoring service 330 via the network 30, 50, 60. As illustrated in FIGS. 3G, H, the monitoring service 330 or monitoring apparatus is communicatively coupled to the practitioner 320 using any of a number of communication techniques know to those skilled in the art. For example, the monitoring apparatus can communicate directly with the practitioner, through the network 30, 50, 60 and/or through the internet 40.

In further embodiments, the network is operably coupled to the internet 40 so that information from the third or fourth exemplary device 310c,d is communicated via the network 30, 50, 60 and internet 40 to the monitoring service 330 or the practitioner 320. In the case where the provided device 300c,d is in a non-clinical setting, for example, the communication interface and device are configurable so that the user can couple the device to the patient's internet connection. The user can be the patient, a person who has not specific medical training or it can be a medically trained person such a visiting nurse or aid. Thus, the acquired information can be transmitted or communicated via that connection to the monitoring service or practitioner.

The foregoing is illustrative of a number of communication techniques; however the foregoing shall not be considered limiting. It is well within the scope of the present invention for those skilled in the communication arts to adapt known or hereinafter developed communication systems and interfaces so that acquired information can be communicated from the device 300 or systems 200a-d according to the present invention to a practitioner or monitoring service or monitoring station.

Figure 1:
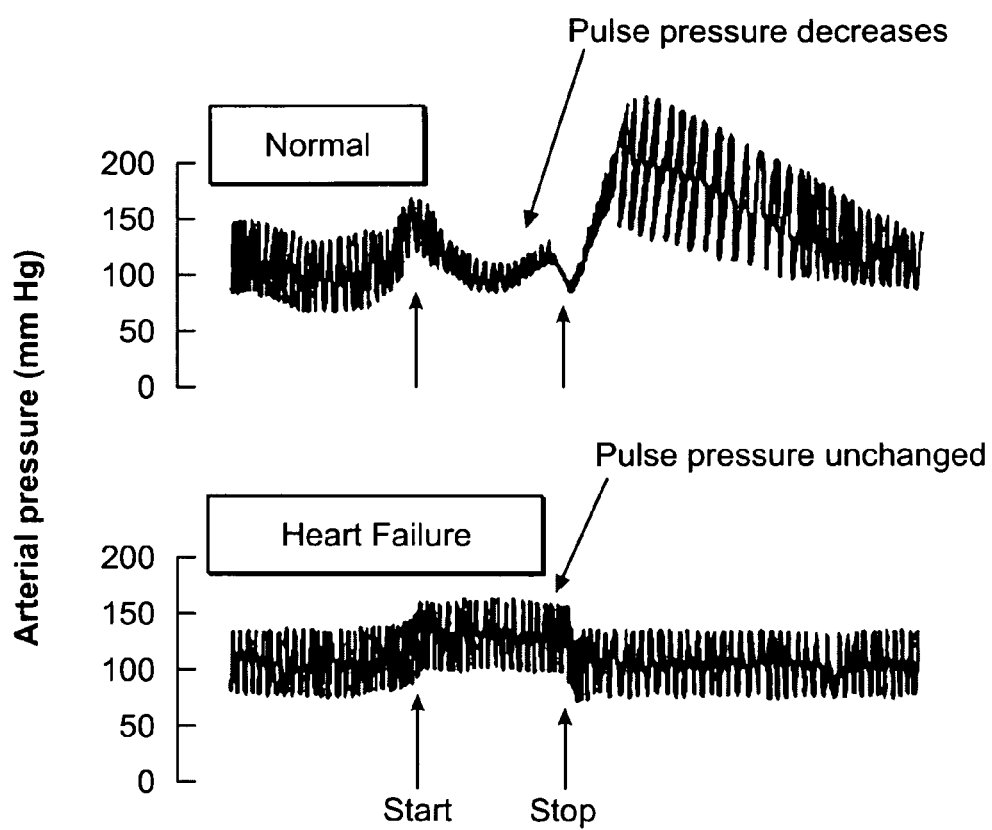
FIG. 1 is a graphical view illustrating the effect of the Valsalva maneuver on blood pressure for a normal heart and a heart with heart failure.

As indicated above, the methodology of the present invention is illustrated in the flow diagram shown in FIG. 1. In the following discussion the reference to a system 200 shall be understood to mean a reference to any of the systems described herein. When the clinician intends to assess the cardiac filing pressure of a patient non-invasively using the system 200 of the present invention, the clinician, technician or medical personnel, provides and arranges the optical pulse volume sensing device 210 on a finger 2 or digit of a patient or subject and so that the optical pulse volume sensing device senses a change in volume caused by the pressure pulse, Step 100, and also provides and fluidly couples a pressure transducer 220 to the patient's mouth 4 so that the pressure transducer thereafter measures expiratory pressure or inspiratory pressure, Step 102. It should be recognized that these steps can be done in any order.

When so arranged the optical pulse volume sensing device 210 such as a PPG, senses a change in volume caused by the pressure pulse by illuminating the skin with light from an LED and then measuring the amount of light either transmitted or reflected to a photodiode. The optical pulse volume sensing device 210 provides an output of a pulse pressure signal of cardiac circulatory flow. As also indicated herein providing and fluidly coupling of the pressure transducer 220 can further include providing a mouth piece and/or tubing, one end of which is fluidly coupled to the patient's mouth. In such a case, the pressure transducer also is disposed in the one of the mouth piece or tubing so the pressure transducer is remote from the mouth.

After so providing, arranging and coupling the optical pulse volume sensing device 210 and the pressure transducer 220, pressure data as a function of time or measurements of the patient's pulse amplitude are acquired using the optical pulse volume sensing device 210, Step 104. In accordance with the specific directions of the medical procedure controlling the assessment process, the patient is directed to breath through the mouth piece and/or tubing 212,214 so as to maintain a desired expiratory pressure for a desired period of time, Step 106. Alternatively, the positive pressure delivery device 280 is controlled so a desired inspiratory pressure is delivered for a predetermined period of time. As indicated herein, a pressure display 260 is provided to assist the patient in maintaining the desired expiratory pressure. While such expiration or positive pressure inspiration is occurring, the expiratory/inspirator pressure is measured or pressure data is acquired as a function of time using the pressure transducer 220, Step 108.

In particular embodiments, the expiratory or positive pressure inspiratory pressure condition (e.g., desired expiratory pressure) is maintained for a period of 10 or more seconds or 10 or less seconds, or about 10 seconds or in the range of from about 8 to about 12 seconds. In yet further particular embodiments, the expiratory or positive pressure inspiratory pressure condition is maintained at about 20 mmHg, or at least 20 mmHg, or in the range of from about 20 mmHg to about 35 mmHg, or in the range of from about 10 mmHg to about 50 mmHg. In the case where a plurality of pulse amplitude ratios are to be obtained (as discussed further herein in connection with Step 110) and where at least one of the plurality pulse amplitude ratios is determined under a different expiratory pressure or a different positive pressure inspiratory pressure; each of the different expiratory/positive pressure inspiratory pressures is in the range of from about 10 mmHg to about 50 mmHg. As indicated herein, the pressure display 260 also can include a display of time or elapsed time so that the patient can maintain the desired expiratory pressure for the specified time period.

As indicated herein, it is within the scope of the present invention to obtain one or more, a plurality or a multiplicity of pressure amplitude ratios under the same expiratory or positive pressure inspiratory pressure conditions or where the expiratory or positive pressure inspiratory pressure conditions differ at least for one of the pulse volume amplitude ratios or per a desired pattern of expiratory pressure conditions. Thus, the specific directions of the medical procedure controlling the assessment process are reviewed initially to determine if more than one pressure amplitude ratio is to be obtained or not. Thus, after the expiratory pressure or positive pressure inspiratory pressure and pulse pressure information or data is acquired, the status of the assessment process is evaluated and a determination is made as to whether the data acquisition process for the intended assessment process is complete, Step 110. If data acquisition is not complete (No, Step 110) then the process continues to repeat Steps 104-108.

If the data acquisition is complete (Yes, Step 110) then the process proceeds to step 112, and the calculation or determination of the pulse amplitude ratio is undertaken, where a pulse amplitude ratio is determined for each of the pressure data acquisitions that were made. The pulse amplitude ratio is determined using the pulse amplitude near the end of the expiratory effort and a baseline pulse amplitude for each of the acquired data sets.

In particular embodiments, the pulse volume of the photoplethysmography waveform from the optical pulse volume sensing device 210, which is the width of the signal from minimum to maximum during one cardiac cycle, is measured. Also, a comparison is made of the pulse volume near the end of the expiratory effort to the pulse volume at baseline before the expiratory or positive pressure inspiratory effort begins. The ratio of the pulse volume near the end of the expiratory or positive pressure inspiratory effort to the pulse volume before the beginning of the expiratory or positive pressure inspiratory effort, which is called the pulse amplitude ratio, is used.

After determining the pulse amplitude ratio(s), an assessment is made to determine if the corresponding cardiac filing pressure is representative of a normal filing pressure, an elevated filing pressure (generally indicative of a problem) or is in a range which does not provide a reliable indication by itself of an elevated filing pressure condition.

In accordance with the method of the present invention, the determined information can be displayed on the output display 250 or via a printing device 240, Step 116. The information being displayed includes but is not limited to the photoplethysmography waveform, the expiratory effort waveform and level, and the pulse amplitude ratio number, as well as words or any combination thereof.

In yet further embodiments, such methods of the present invention further includes acquiring information that relates to central arterial stiffness and assessing such acquired information to determine arterial stiffness for the patient. Such methods further includes factoring such arterial stiffness information along with the assessment of the pulse amplitude ratio.

In further embodiments, such methods of the present invention include providing a microprocessor or a computer including such a microprocessor and communicatively coupling the microprocessor to each of the pressure transducer and the optical pulse volume sensing device (e.g., PPG). The provided microprocessor determines the pulse amplitude ratio from the signals from the pressure transducer and the optical pulse volume sensing device (e.g., PPG).

In yet further embodiments, such methods further providing an applications program including program or code segments and instructions and criteria for carrying out the methods of the present invention, including determining the pulse amplitude ratio on demand, automatically and/or periodically. In further embodiments, such an applications program includes program segments and instructions and criteria for causing the periodically determined pulse amplitude ratios as well as any other data such as the pulse amplitude near the end of the expiratory effort, the baseline pulse amplitude and measured expiratory pressures, to be stored in a storage device.

In yet further embodiments, such methods further include providing a device including an enclosure, the microprocessor and storage device, where the microprocessor and storage device are disposed within the enclosure so that the device is one of free-standing, on a rolling cart or portable so as for example, the device can be carried in the pocket of a jacket worn by the clinician, technician or medical personnel.

In yet further embodiments, such a device is arranged so as to include one of a display or a printing device so that determined information is one of displayed to the user or a hard copy of the determined information can be printed out for the user. In more particular embodiments, such displaying or printing is done one of automatically or in response to an input from the user.

In more particular embodiments, the device includes means for communicatively coupling the device microprocessor to each of the optical pulse pressuring sensing device and the pressure transducer.

In yet further embodiments, the provided device includes means for communicatively coupling the device to a communication system (e.g., telephone system, network, internet) for communication the acquired information to the practitioner or a service for monitoring for such communications. Such monitoring services include storing the acquired information and/or for re-transmitting such information onto the practitioner.

In yet further embodiments, such methods include acquiring information using the provided device in clinical and non-clinical settings and transmitting the acquired information via a communication system to the practitioner and/or monitoring service. In more particular embodiments, such methods further include having a person not having medical training (e.g., patient) use the device to acquiring information, couple the device to a communication system and transmit the so acquired information via the communication system to the practitioner and/or monitoring service.

Figure 4:
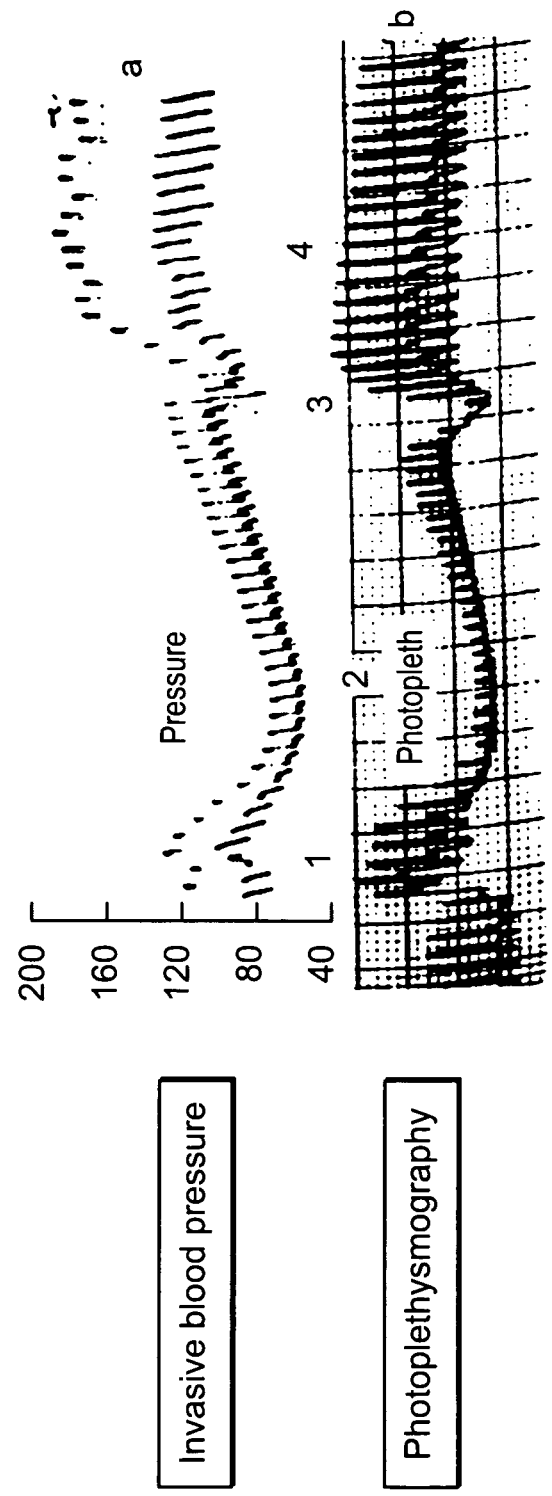
FIG. 4 is graphical view of a photoplethysmography signal and of invasively measured blood pressure during the Valsava maneuver.

Referring now to FIG. 4 there is shown a graphical view of a photoplethysmography signal and of invasive blood pressure during the Valsava maneuver.

Figure 5:
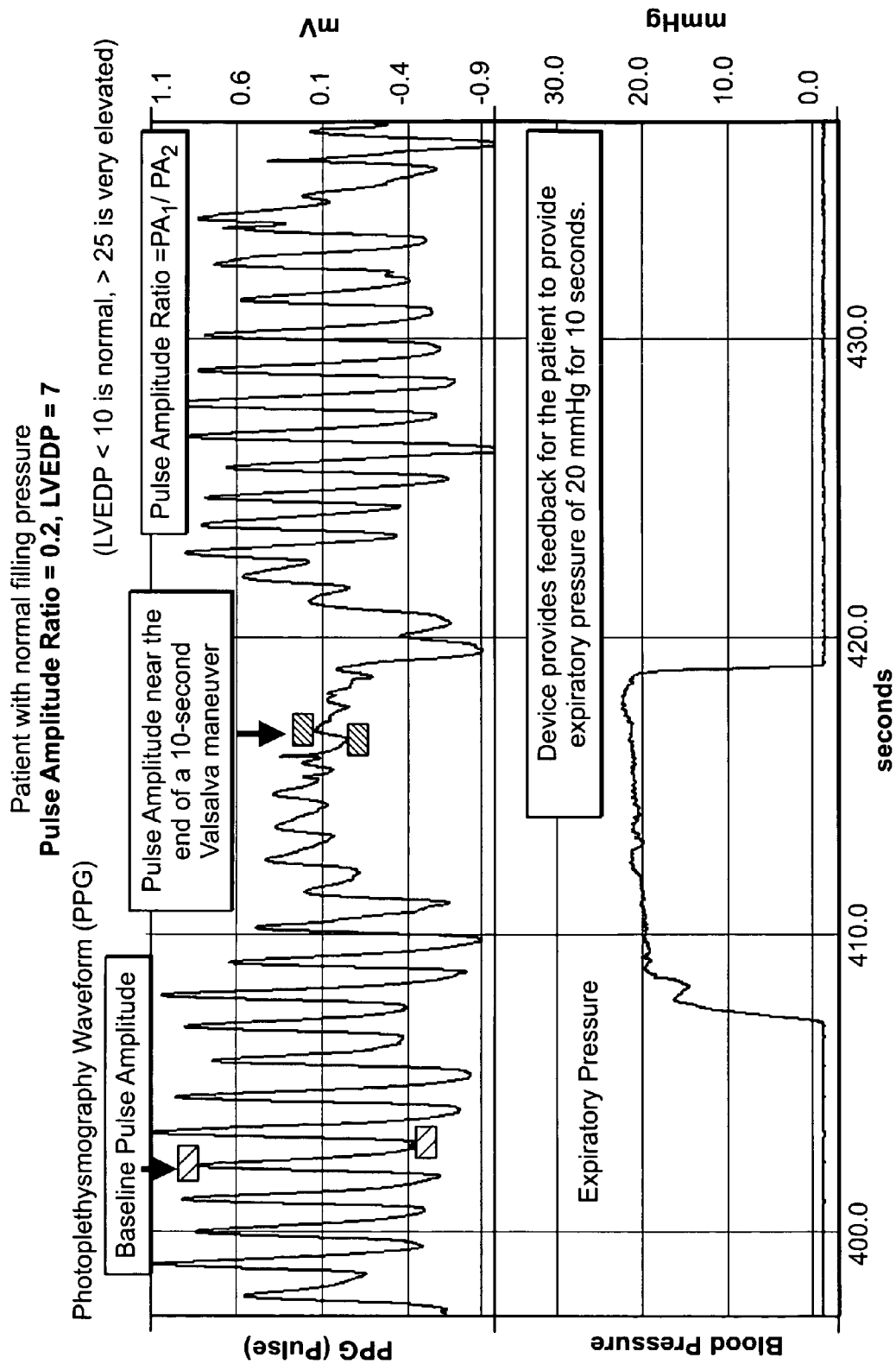
FIG. 5 is a graphical view of a photoplethysmography waveform and the expiratory pressure waveform for a heart with a normal filing pressure using the system of the present invention.

Referring now to FIG. 5 there is shown a graphical view of a photoplethysmography waveform and the expiratory pressure waveform for a heart with a normal filing pressure. As shown therein, using the methods and systems of the present invention, the determined pulse amplitude ratio equals 0.2 and the LVEDP equals 7.

Figure 6:
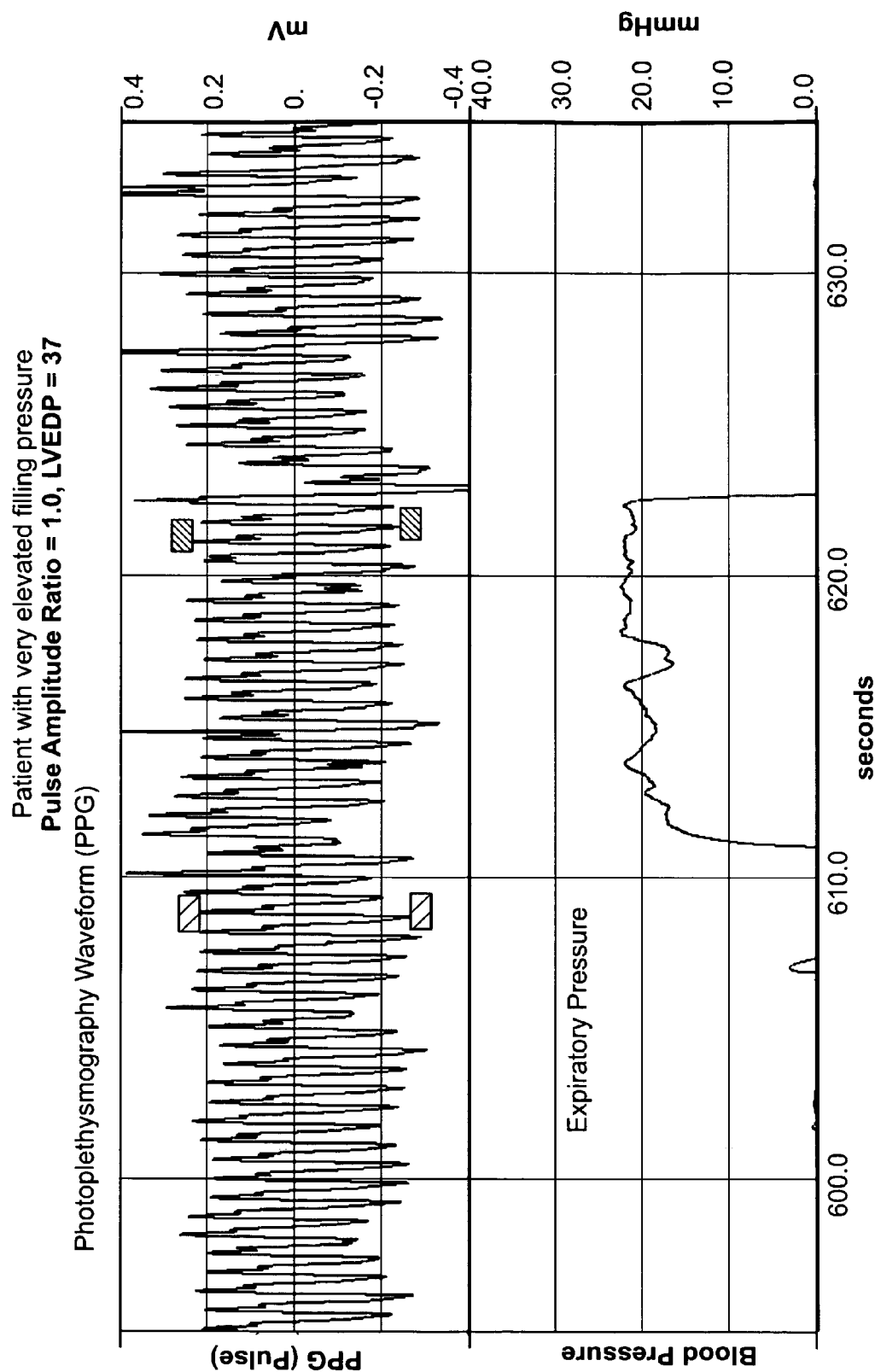
FIG. 6 is a graphical view of a photoplethysmography waveform and the expiratory pressure waveform for a heart with an elevated filing pressure using the system of the present invention.

Referring now to FIG. 6 there is shown a graphical view of a photoplethysmography waveform and the expiratory pressure waveform for a heart with an elevated filing pressure using the system of the present invention. As shown therein, using the methods and systems of the present invention, the determined pulse amplitude ratio equals 1.0 and the LVEDP equals 37.

Figure 7:
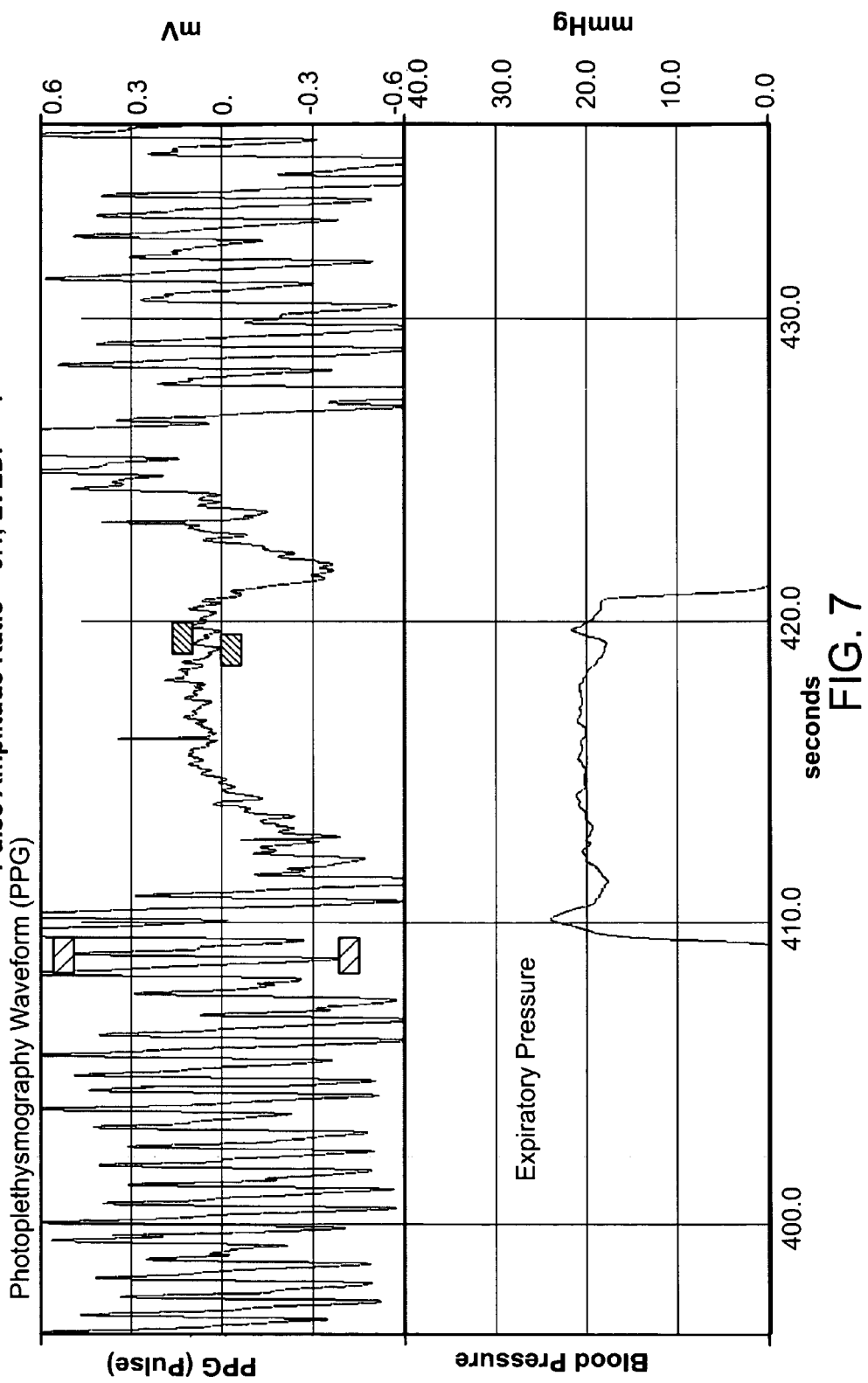
FIG. 7 is a graphical view of a photoplethysmography waveform and the expiratory pressure waveform for a heart of a patient that had been initially diagnosed as being fluid overloaded, but which it was later determined that the heart had a normal filing pressure using the system of the present invention.

Referring now to FIG. 7 there is shown a graphical view of a photoplethysmography waveform and the expiratory pressure waveform for the heart of a patient that had been initially diagnosed as being fluid overloaded, but which was later determined that the heart had a normal filing pressure using the system of the present invention. As shown therein, using the methods and systems of the present invention, the determined pulse amplitude ratio equals 0.1 and the LVEDP equals 4.

Figure 8:
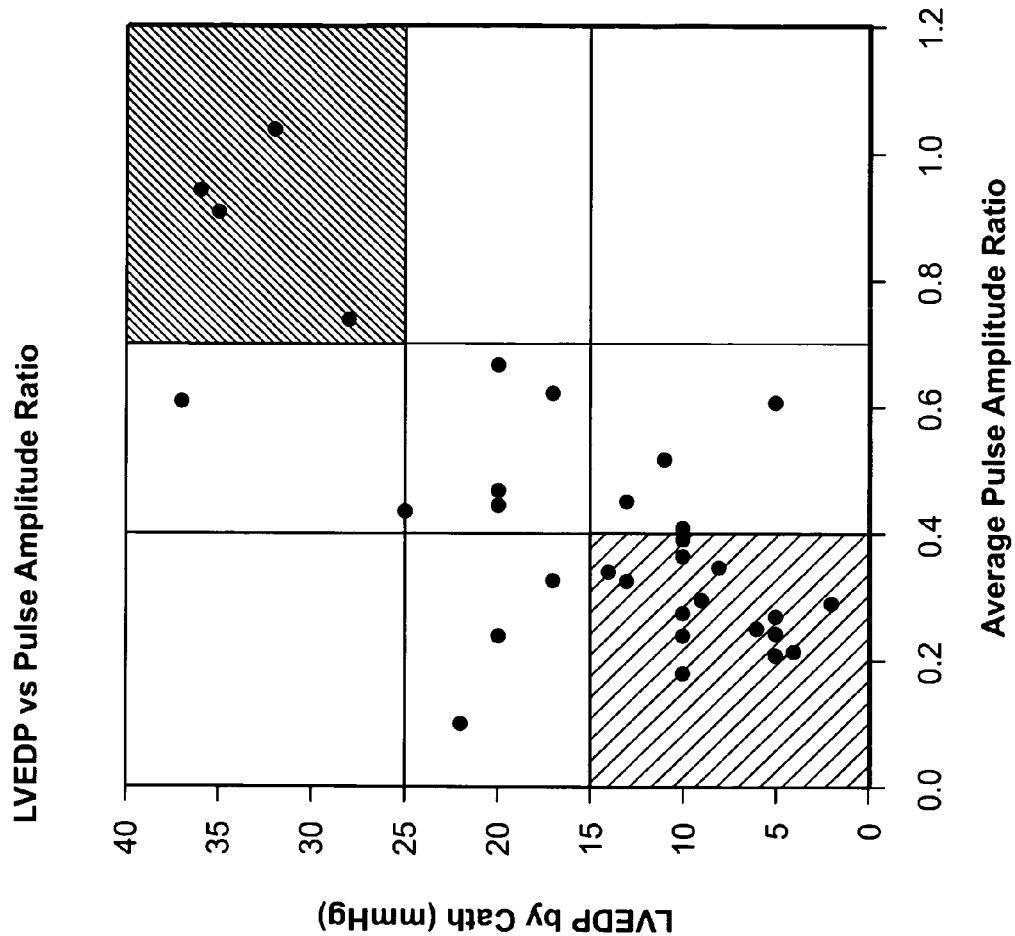
FIG. 8 is a graphical view of LVEDP by catheter versus Average Pulse Amplitude Ratio for a patient study, where the pulse amplitude ratios were determined using the system of the present invention.

Referring now to FIG. 8 there is shown a graphical view of LVEDP by catheter versus Average Pulse Amplitude Ratio for a patient study, where the pulse amplitude ratios were determined using the system of the present invention.

Although a preferred embodiment of the invention has been described using specific terms, such description is for illustrative purposes only, and it is to be understood that changes and variations may be made without departing from the spirit or scope of the following claims.

INCORPORATION BY REFERENCE

All patents, published patent applications and other references disclosed herein are hereby expressly incorporated by reference in their entireties by reference.

EQUIVALENTS

Those skilled in the art will recognize, or be able to ascertain using no more than routine experimentation, many equivalents of the specific embodiments of the invention described herein. Such equivalents are intended to be encompassed by the following claims.

What is claimed is:

1. A method, comprising:
displaying to the user (1) a target expiratory pressure for the user, (2) a target time period for maintaining by the user the target expiratory pressure, and (3) a representation of a target location for the user to place an optical pulse volume sensing device;
sensing a change in pulse volume using the optical pulse volume sensing device coupled to a finger of the user, the optical pulse volume sensing device including a photoplethysmography (PPG) transducer, the optical pulse volume sensing device configured to sense a change in volume caused by a volume pulse by illuminating skin with light from a light emitting diode (LED), and is configured to provide an output of a pulse pressure signal of cardiac circulatory flow;
measuring an expiratory pressure for a predetermined period of time using a pressure transducer fluidly coupled to a mouth;
determining a pulse amplitude ratio, which is a ratio of the pulse amplitude near an end of the predetermined period of time and a baseline pulse amplitude; and
assessing the determined pulse amplitude ratio based on a correlation to determine a filling pressure condition of a heart, the correlation being associated with a graphical plot of a plurality of left ventricular end diastolic pressure (LVEDP) measurements of a plurality of patients using a catheter, and a graphical plot of the plurality of LVEDP measurements against a plurality of pulse amplitude ratios of the plurality of patients.

2. The method of claim 1, wherein the pressure transducer is disposed in one of a mouth piece or a tubing so the pressure transducer is located remote from the mouth.

3. The method of claim 1, further comprising:
communicatively coupling a microprocessor to each of the pressure transducer and the optical pulse volume sensing device; and
determining the pulse amplitude ratio includes determining the pulse amplitude ratio using the microprocessor and output signals from the pressure transducer and the optical pulse volume sensing device.

4. The method of claim 3, wherein the microprocessor includes an applications program including program segments and instructions and criteria for determining the pulse amplitude ratio from the output signals from the pressure transducer and the optical pulse volume sensing device.

5. The method of claim 4, wherein the applications program includes program segments and instructions and criteria for periodically deter mining the pulse amplitude ratio.

6. The method of claim 4, further comprising:
storing in a storage device operably coupled to said microprocessor the determined pulse amplitude ratios, a pulse volume near the end of the predetermined period of time, the baseline pulse volume and measured pressures during the predetermined period of time.

7. The method of claim 3, further comprising:
printing data associated with the determined pulse amplitude ratios using a printing device operably coupled to said microprocessor.

8. The method of claim 6, further comprising:
disposing the microprocessor and storage device in an enclosure of a device.

9. The method of claim 8, wherein the device further includes one of a display device or a printing device; and wherein said method further includes one of displaying determined information using the display device or outputting a hard copy of the determined information.

10. The method of claim 8, wherein the device microprocessor is communicatively coupled to each of the optical pulse volume sensing device and the pressure transducer.

11. The method of claim 1, wherein:
the optical pulse volume sensing device further includes a communication interface module that is configured to form a communication link with a communications system that is external to said device and to output signals to the communications system that are appropriate for transmission over the communications system.

12. The method of claim 11, further comprising communicating information acquired by the optical pulse volume sensing device to one of a practitioner or a monitoring apparatus.

13. A system for assessing cardiac filling pressure non-invasively, said system comprising:
a display module configured to display to a user (1) a target expiratory pressure for the user, (2) a target time period for maintaining by the user the target expiratory pressure, and (3) a representation of a target location for the user to place an optical pulse volume sensing device;
the optical pulse volume sensing device including a photoplethysmography (PPG) transducer, the optical pulse volume sensing device configured to be located on a finger or digit of the user such that the optical pulse volume sensing device senses a change in volume caused by a pressure pulse by illuminating skin with light from a light emitting diode (LED), the optical pulse volume sensing device configured to provide an output of a pulse pressure signal of cardiac circulatory flow;
a pressure transducer configured to be fluidly coupled to a mouth such that the pressure transducer measures expiratory pressure during a predetermined period of time; and
a processor configured to determine a pulse amplitude ratio, which is a ratio of the pulse pressure near an end of the predetermined period of time and a baseline pulse pressure; and
an output device configured to display the pulse amplitude ratio based on the correlation to determine a filling pressure condition for a heart, the correlation being associated with a graphical plot of a plurality of left ventricular end diastolic pressure (LVEDP) measurements of a plurality of patients using a catheter, and a graphical plot of the plurality of LVEDP measurements against a plurality of pulse amplitude ratios of the plurality of patients.

14. A device for assessing cardiac filling pressure non-invasively, said device comprising:
an optical pulse volume sensing device including a photoplethysmography (PPG) transducer, the optical pulse volume sensing device configured to be located on a finger or digit such that the optical pulse volume sensing device senses a change in volume caused by a pressure pulse by illuminating skin of the finger or digit with light from a light emitting diode (LED), the optical pulse volume sensing device configured to provide an output of a pulse pressure signal of cardiac circulatory flow;
a microprocessor configured to be communicatively coupled to the optical pulse volume sensing device and to a pressure transducer that is fluidly coupled to a mouth such that the pressure transducer measures expiratory pressure during a predetermined period of time, the pressure transducer operatively coupled to a display module configured to display to a user (1) a target expiratory pressure for the user, (2) a target time period for maintaining by the user the target expiratory pressure, and (3) a representation of a target location for the user to place the optical pulse volume sensing device; and
an applications program for execution on the microprocessor, the applications program including program segments and instructions and criteria for determining a pulse amplitude ratio, which is a ratio of the pulse volume near an end of the predetermined period of time and a baseline pulse volume; and for determining a correlation between the pulse amplitude ratio and left ventricular end diastolic pressure (LVEDP) based on a graphical plot of a plurality of LVEDP measurements of a plurality of patients using a catheter and a graphical plot of the plurality of LVEDP measurements against a plurality of pulse amplitude ratios of the plurality of patients; and
for assessing the determined pulse amplitude ratio based on the correlation so as to determine a filling pressure condition for the heart of the patient.

15. A method for assessing cardiac filling pressure non-invasively, said method comprising:
displaying to the user a representation of a target location for the user to place an optical pulse volume sensing device, the optical pulse volume sensing device including a photoplethysmography (PPG) transducer;
sensing, using the optical pulse volume sensing device operably coupled to a finger or a digit of a patient or subject, a change in volume caused by a pressure pulse by illuminating skin with light from a light emitting diode (LED), the optical pulse volume sensing device configured to provide an output of a pulse pressure signal of cardiac circulatory flow;
providing a positive pressure delivery device;
fluidly coupling a pressure transducer to the patient's mouth;
selectively fluidly coupling the positive pressure delivery device to the patient's mouth so as to maintain a positive inspiratory pressure condition of about 20 mmHg to about 35 mmHg for about 8 to about 12 seconds;
determining a pulse amplitude ratio while the positive inspiratory pressure condition is maintained, which is a ratio of the pulse amplitude near the end of the predetermined period of time and a baseline pulse amplitude; and determining a correlation between the determined pulse amplitude ratio and filling pressure, and using the correlation so as to determine a filling pressure condition for the heart of the patient.

16. The method of claim 1, wherein said fluidly coupling a pressure transducer to the patient's mouth so that the pressure transducer measures an expiratory pressure further comprises maintaining an expiratory pressure condition in the range of from about 20 mmHg to about 35 mmHg.

17. The method of claim 16, wherein the expiratory pressure condition is maintained at about 20 mmHg for about 8 seconds to about 12 seconds.

18. The method of claim 1, wherein the determined correlation is a pulse amplitude ratio of less than or equal to 0.4 indicates a LVEDP of less than or equal to 15 or a pulse amplitude ratio of greater than or equal to 0.7 indicates a LVEDP of greater than or equal to 25.

* * * * *

UNITED STATES PATENT AND TRADEMARK OFFICE
CERTIFICATE OF CORRECTION

PATENT NO. : 9,549,678 B2  
APPLICATION NO. : 13/003076  
DATED : January 24, 2017  
INVENTOR(S) : Harry A. Silber Page 1 of 1

It is certified that error appears in the above-identified patent and that said Letters Patent is hereby corrected as shown below:

In the Claims

Column 16, Line 66 (Claim 5, Line 3):
"deter mining" should be --determining--

Signed and Sealed this
Twenty-second Day of August, 2017

Joseph Matal
*Performing the Functions and Duties of the*
*Under Secretary of Commerce for Intellectual Property and*
*Director of the United States Patent and Trademark Office*